US007371371B2

(12) United States Patent
Epstein et al.

(10) Patent No.: US 7,371,371 B2
(45) Date of Patent: May 13, 2008

(54) INTERLEUKIN-2 MUTANTS WITH REDUCED TOXICITY

(75) Inventors: Alan L. Epstein, La Canada, CA (US); Peisheng Hu, Covina, CA (US)

(73) Assignee: University of Southern California, Los Angeles, CA (US)

( * ) Notice: Subject to any disclaimer, the term of this patent is extended or adjusted under 35 U.S.C. 154(b) by 828 days.

(21) Appl. No.: 10/218,197

(22) Filed: Aug. 12, 2002

(65) Prior Publication Data

US 2003/0124678 A1 Jul. 3, 2003

Related U.S. Application Data

(60) Provisional application No. 60/312,326, filed on Aug. 13, 2001.

(51) Int. Cl.
*A61K 38/20* (2006.01)
*C07K 14/55* (2006.01)

(52) U.S. Cl. ..................... 424/85.2; 530/351

(58) Field of Classification Search ............... 530/351, 530/402; 424/85.2; 514/2, 8, 12
See application file for complete search history.

(56) References Cited

U.S. PATENT DOCUMENTS

| | | | |
|---|---|---|---|
| 4,604,377 A | 8/1986 | Fernandes et al. | |
| 4,766,106 A | 8/1988 | Katre et al. | |
| 4,959,314 A | 9/1990 | Mark et al. | |
| RE33,653 E | 7/1991 | Mark et al. | |
| 5,116,943 A | 5/1992 | Koths et al. | |
| 5,116,964 A * | 5/1992 | Capon et al. ............. | 536/23.5 |
| 5,206,344 A | 4/1993 | Katre et al. | |
| 5,498,530 A | 3/1996 | Schatz et al. | |
| 5,565,332 A | 10/1996 | Hoogenboom et al. | |
| 5,837,500 A | 11/1998 | Ladner et al. | |
| 5,969,108 A | 10/1999 | McCafferty et al. | |
| 6,008,319 A | 12/1999 | Epstein et al. | |
| 6,348,192 B1 | 2/2002 | Chan et al. | |

FOREIGN PATENT DOCUMENTS

| | | |
|---|---|---|
| JP | 60126088 | 7/1985 |
| WO | WO 87/00056 | 1/1987 |
| WO | WO 93/20849 | 10/1993 |

OTHER PUBLICATIONS

Callard and Gearing (1994), The Cytokine Factsbook, Academic Press Ltd., pp. 39-40.*
Ruoff et al.. Development of low-toxicity IL-2 analogs for the immunotherapy of solid tumors. Proceedings for the American Association for Cancer Research Annual Meeting. 40: p. 76, Mar. 1999.*
Allegretta et al., "The Development of anti-interlerkin-2 antibodies in patients treated with recombinant human interleukin-2 (IL-2)," Journal of Clinical Immunology, 6(6): 481-490, 1986.
Bergmann et al., "Phase separation analysis of recombinant interleukin 2," Molecular Immunology, 28(1): 99-105, 1991.
Buttke et al., "Use of an aqueous solube tetrazolium/formazan assay to measure viability and proliferation of lymphokine-dependent cell lines," Journal of Immunological Methods, 157: 233-240, 1993.
Cotran et al., "Endothelial activation during interleukin 2 immunotherapy," The Journal of Immunology, 139: 1883-1888, 1987.
Eckenberg et al., "Analysis of human IL-2/IL-2 receptor βchain interactions: Monoclonal antibody h2-8 and new IL-2 mutants define the critical role of α helix-A and IL-2," Cytokine, 9(7): 488-498, 1997.
Farner et al., "Distinction between $\gamma_c$ detection and function in YT lymphoid cells and in the granulocyte-macrophage colony-stimulating factor-responsive human myeloid cell line, Tf-1," Blood, 86(12): 4568-4578, 1995.
Frankel et al., "The Rapid determination of binding constants for antiviral antibodies by a radioimmunoassay. An analysis of the interaction between hybridoma proteins and influenza virus," Mol. Immun., 16:101-106, 1979.
Gieni et al., "Comparison of [3H]thymidine incorporation with MTT- and MTS-based bioassayss for human and murine IL-2 and IL-4 analysis Tetrazolium assays provide markedly enhanced sensitivity," Journal of Immunological Methods, 187:85-93, 1995.
Hornick et al., "A New Chemically Modified Chimeric TNT-3 Monoclonal Antibody Directed Against DNA for the Radioimmunotherapy of solid tumors," Cancer Biotherapy & Radiopharmaceuticals, 13(14): 255-268, 1998.
Hornick et al., "Single amino acid substitution in the Fc region chimeric TNT-3 antibody accelerates clearance and improves immunoscintigraphy of solid tumors," J.Nucl.Med., 41:355-362, 2000.
Huse et al., "Generation of a large combinatorial library of the immunoglobulin repertoire in phage lambda," Science, 246:1275-1281, 1989.
Lam et al., "A new type of synthetic peptide library for identifying ligand-binding activity," Nature, 354: 82-84, 1991.
LeBerthon et al., "Enhanced tumor uptake of marcomolecules induced by a novel vasoactive interleukin 2 immunoconjugate," Cancer Research, 51:2694-2698, 1991.
Marks et al., "Characterization and responsiveness of the Madison 109 lung carcinoma to various antitumor agents," Cancer Treatment Reports, 61(8): 1459-1470, 1977.
Oda et al., "Induction of IL-1β-converting enzyme-independent apoptosis by IL-2 in human T cell lines," International Immunology, 9(9): 1303-1310, 1997.

(Continued)

*Primary Examiner*—Prema M. Mertz
(74) *Attorney, Agent, or Firm*—Foley & Lardner, LLP

(57) ABSTRACT

Interleukin-2 (IL-2) mutants having reduced toxicity, which include full-length IL-2, truncated forms of IL-2 and forms of IL-2 that are linked to another molecule are disclosed herein. Particular substitutions within IL-2, particularly within the permeability enhancing peptide region of IL-2 achieve substantial reduction of vasopermeability activity as compared to a wildtype form of the mutant IL-2 while retaining many of the immune activating properties of IL-2. Invention IL-2 mutants can be used to stimulate the immune system of an animal and may be used in the treatment of various disorders and conditions.

11 Claims, 9 Drawing Sheets

OTHER PUBLICATIONS

Ohsugi et al., "Tumorigenicity of human malignant lymphoblasts: Comparative study with unmanipulated nude mice, antilymphocyte serum-treated nude mice, and X-irradiated nude mice," JNCL, 63(4): 715-718, 1980.

Rong et al., "Analysis of IL-2 functional structure by multiple cysteine substitutions," Biochemical and Biophysical Research Communications, 188(2): 949-955, 1992.

Shanafelt et al., "A T-cell-selective interleukin 2 mutein exhibits potent antitumor activity and is well tolerated in vivo," Nature Biotechnology, 18:1197-1202, 2000.

Shipley et al., "Regulation of growth of an interleukin 2(IL-2)-dependent murine T-cell clone (HT-2) in a defined serum-free medium," Cellular Immunology, 93:459-466, 1985.

Taniguchi et al., "Structure and expression of a cloned cDNA for human interleukin-2," Nature, 302:305-310, 1983.

Theze et al., "Interleukin 2 and its receptors: recent advances and new immunological functions," Immunology Today, 17:481-486, 1996.

Tom et al., "Human colonic adenocarcinoma cells," In Vitro, 12(3): 180-191, 1976.

Tsudo et al., "Reconstitution of a functinal IL-2 receptor by the β-chain cDNA," Journal of Immunology, 143:4039-4043, 1989.

Weigel et al., "Mutant proteins of human interleukin 2: Renaturation yield, proliferative and receptor binding," Eur. J. Biochem., 180:295-300, 1989.

Yodoi et al., "TCGF (IL 2)-receptor inducing factors(s): Regulation of IL 2 receptor on a natural killer-like cell in (YT cells)," The Journal of Immunology, 134: 1623-1630, 1985.

Supplementary Partial European Search Report for EP Application No. 02 75 2821.

Cassell et al. Therapeutic Enhancement of IL-2 through Molecular Design. Current Pharmaceutical Design, 8:2171-2183, 2002.

Epstein et al., Identification of a Protein Fragment of Interlerkin 2 Responsible for Vasopermeability. Journal of the National Cancer Institute, 95(10): 741-749, 2003.

Heaton et al., Human Interleukin 2 Analogues that Preferentially Bind the Intermediate-Affinity Interleukin 2 Receptor Lead to Reduced Secondary Cytokine Secretion: Implications for the Use of These Interleukin 2 Analogues in Cancer Immunotherapy. Cancer Research, 53: 2597-2602, 1993.

Heaton et al., Induction of Lymphokine-Activated Killing with Reduced Secretion of Interleuking-1β, Tumor Necrosis Factor-α, and Interferon-γ by Interluekin-2 Analogs. Annals of Surgical Oncology. 1(3): 198-203, 1994.

Hu et al., Generation of low-toxicity interleukin-2 fusion proteins devoid of vasopermeability activity. Blood, 101(12): 4853-4861, 2003.

Ju et al, Structure-Function Analysis of Human Interleukin-2. The Journal of Biological Chemistry. 262:5723-5731, 1967.

Ruoff et al., Developement of low-toxicity IL-2 analogs for the immunotherapy of solid tumors. Proceedings for the American Association for Cancer Research Annual Meeting, 40: p. 76, Mar. 1999.

Sauve et al., Localization in human interleukin 2 of the binding site to the α chain (p55) of the interleukin 2 receptor. Proc. Nat. Acad. Sci. USA, 88: 436-4640, Jun. 1991.

A Poster Presentation on Interleukin-2 (IL-2) from the 1999 AACR meeting, p. 1-7, Ruoff et al.

* cited by examiner

```
                    5              10              15              20
AlaProThrSerSer  SerThrLysLysThr  GlnLeuGlnLeuGlu  HisLeuLeuLeuAsp
      25              30              35              40
LeuGlnMetIleLeu  AsnGlyIleAsnAsn  TyrLysAsnProLys  LeuThrArgMetLeu
      45              50              55              60
ThrPheLysPheTyr  MetProLysLysAla  ThrGluLeuLysHis  LeuGlnCysLeuGlu
      65              70              75              80
GluGluLeuLysPro  LeuGluGluValLeu  AsnLeuAlaGlnSer  LysAsnPheHisLeu
      85              90              95             100
ArgProArgAspLeu  IleSerAsnIleAsn  ValIleValLeuGlu  LeuLysGlySerGlu
     105             110             115             120
ThrThrPheMetCys  GluTyrAlaAspGlu  ThrAlaThrIleVal  GluPheLeuAsnArg
     125             130             135             140
TrpIleThrPheCys  GlnSerIleIleSer  ThrLeuThr---
```

Figure 9

SEQUENCE LISTING

<160> NUMBER OF SEQ ID NOS: 15

<210> SEQ ID NO 1
<211> LENGTH: 32
<212> TYPE: DNA
<213> ORGANISM: Artificial Sequence
<220> FEATURE:
<221> NAME/KEY: CDS
<222> LOCATION: (1)..(32)
<220> FEATURE:
<223> OTHER INFORMATION: Description of Artificial Sequence: Synthetic
      linker oligonucleotide

<400> SEQUENCE: 1 ggt aaa gcg gcc gca gga ggt ggt agc gca cc                         32
Gly Lys Ala Ala Ala Gly Gly Gly Ser Ala Pro
  1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Gly Lys Ala Ala Ala Gly Gly Gly Ser Ala Pro
  1               5                  10

<210> SEQ ID NO 3
<211> LENGTH: 133
<212> TYPE: PRT
<213> ORGANISM: Homo sapiens

<400> SEQUENCE: 3

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
ttactgctga aattacagat g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
catctgtaat ttcagcagta a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
aaactcacck ggatgctcac a                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
tgtgagcatc cmggtgagtt t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
ctcaccaggs tgctcacatt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
aaatgtgagc ascctggtga g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer
```

```
<400> SEQUENCE: 10
atgctcacaa agaagtttta c                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
gtaaaacttc tttgtgagca t                                                 21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
gaactgaaat aatcttcagt gt                                                22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
acactgaaga tatatttcag ttc                                               23

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 14
ggtaaagcgg ccgcaggagg tggtagcgca cctacttcaa gttctaca                    48

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 15
tcatgcggcc gctcaagtta gtgttgagat gatgct                                 36
```

INTERLEUKIN-2 MUTANTS WITH REDUCED TOXICITY

CROSS REFERENCE TO RELATED PATENT APPLICATIONS

This application is a Non-Provisional of U.S. Application 60/312,326, filed Aug. 13, 2001, incorporated herein by reference in its entirety.

FIELD OF THE INVENTION

The present invention relates to the use of interleukin-2 (IL-2) as an immunotherapeutic agent and to IL-2 mutants that exhibit reduced vasopermeability and reduced toxicity compared to native IL-2.

BACKGROUND OF THE INVENTION

Cytokines play a role in the growth and differentiation of all cells in the body but are especially important to cells of the immune system. A category of cytokines are called interleukins, of which 18 have been identified thus far. Interleukin-2 (IL-2) is an important cytokine for the regulation of T-cell function in the immune system. Because of its important involvement in both the cellular and humoral arms of the immune system, IL-2 has been investigated extensively for a potential role in the treatment of disease. Although the primary function of IL-2 is to stimulate the growth and proliferation of T lymphocytes, IL-2 is also known to have diverse stimulatory effects on a variety of immune cells, including natural killer (NK) cells, lymphokine-activated killer (LAK) cells, monocytes, and macrophages. In regulating the immune system, IL-2 also may trigger the production of secondary cytokines, such as interferons and TNF-α, to further stimulate an immune response. Interferons, interleukins and TNF-α can be made in mass quantities through recombinant techniques for therapeutic applications.

IL-2 administration is a therapeutic treatment in cancer and other diseases. For example, IL-2 is approved for the treatment of metastatic renal cell carcinoma and melanoma. In this setting, intravenous IL-2 produces a 20% rate of remission. However the efficacy of IL-2 has been restricted by the relatively severe toxicities associated with therapeutic dosages. The native form of IL-2 exhibits toxic side effects that may include myocardial infarction, renal failure requiring dialysis, fluid retention, nausea and neuropathy. In addition, IL-2 administration is associated with generalized inflammatory changes which include the development of dose limiting capillary leak syndrome. The short half-life of i.v. administered IL-2 (about 22 minutes) requires the higher dosing that leads to toxicity.

Attempts to reduce the unwanted toxicity associated with the therapeutic use of IL-2 have focused on increasing the half-life of the molecule. This has been achieved by increasing the molecular size by linking IL-2 to another molecule such as a protein or polymer, or by linking IL-2 to a targeting molecule such as an antibody. Attempts to direct IL-2 to the site of disease by a targeting molecule have been somewhat effective and have resulted in increased levels of therapeutic efficacy, including control of malignant effusions, prevention of the growth of established tumors, and even a reduction in the size of established tumors. However, such approaches cannot be used in all anatomic locations and are not applicable to disseminated disease.

IL-2 molecules that have a mutated amino acid sequence through substitution of amino acid residues present in the wildtype IL-2 molecule have been reported to have reduced toxicity. However, such mutants are associated with altered biological function such as reduced binding affinity to forms of the IL-2 cellular receptor and altered cytokine functions, including T cell stimulation, LAK or natural killer cell activation, or secondary cytokine production. Therefore, there remains a need in the art for a low toxicity variant of IL-2 to minimize toxicities associated with treatment.

BRIEF SUMMARY OF THE INVENTION

In accordance with the present invention, novel IL-2 mutants with reduced toxicity as compared to native IL-2 are presented. Such mutants are characterized by substantially reduced vasopermeability activity and substantially similar binding affinity for an IL-2 receptor compared to a wildtype form of the IL-2 mutant. By reducing the vasopermeability activity of the IL-2, the present invention meets the need in the art for a low toxicity variant of IL-2 that avoids toxic side effects such as vascular leak syndrome. Thus, in one aspect of the present invention, the IL-2 mutant can be used to stimulate the immune system of an animal to achieve maximal therapeutic benefit with reduced side effects.

Invention IL-2 mutants comprise at least one mutation in the permeability enhancing peptide region of IL-2. In one embodiment, the IL-2 mutant is derived from human IL-2. In another embodiment, the IL-2 mutant comprises one or more non-wildtype amino acid residues located at positions 22-58 of IL-2. Preferred substitutions include $W_{38}$, $G_{38}$, $Y_{38}$, $L_{39}$, $K_{42}$ and $Y_{55}$. The invention IL-2 mutants may be full length IL-2 or fragments of IL-2 and may be linked to another molecule. The above IL-2 mutants also may include select mutations outside the permeability enhancing peptide region of IL-2.

Also provided is a method for identifying interleukin-2 (IL-2) mutants with reduced toxicity, the method comprising assaying IL-2 mutants comprising a mutation in the permeability enhancing peptide region of IL-2 for vasopermeability activity and for binding affinity for an IL-2 receptor, the mutants with reduced toxicity characterized by substantially reduced vasopermeability and similar binding affinity for an IL-2 receptor as compared to a wildtype form of the IL-2 mutant.

Further provided is a method of producing a low toxicity IL-2 in a form suitable for administration in vivo, the method comprising:
   a) obtaining a mutant IL-2 characterized by substantially reduced vasopermeability activity and substantially similar binding affinity for an IL-2 receptor compared to a wildtype form of the IL-2 mutant; and
   b) formulating the mutant IL-2 with at least one pharmaceutically acceptable carrier, whereby a preparation of low toxicity IL-2 is formulated for administration in vivo. Still further provided is method for stimulating the immune system of a subject in need thereof, the method comprising administering an effective amount of an interleukin-2 (IL-2) mutant to the subject, the mutant comprising a mutation in the permeability enhancing peptide region of IL-2, the mutant characterized by substantially reduced vasopermeability activity and substantially similar binding affinity for an IL-2 receptor compared to a wildtype form of the IL-2 mutant. Such mutants can be used as an immunotherapeutic agent in the treatment of cancers such as renal cell carcinoma or melanoma, in the treatment of immune deficiencies such as from viral infection including infection by an immunodeficiency virus, chemotherapy and/or radiation therapy, or in the treatment of autoimmune disorders.

BRIEF DESCRIPTION OF THE DRAWINGS

These and other features, aspect, and advantages of the present invention will become better understood with regard to the detailed description, claims and figures provided herein.

FIG. 4A represents interleukin-1β (IL-1β) production. FIG. 4B represents interferon-γ (IFN-γ) production. FIG. 4C represents tumor necrosis factor-α (TNF-α) production.

FIG. 5A depicts the R38 mutants. FIG. 5B depicts the M39 mutants. FIG. 5C depicts the D20, F42, and H55 mutants.

FIG. 6A shows mice receiving chTNT-3/IL-2 (5-20 μg) as compared to no treatment. FIG. 6B shows mice receiving chTNT-3/IL-2 (5-50 μg) as compared to no treatment.

FIG. 7A shows mice receiving chTNT-3/R38W protein (5-20 μg) as compared to no treatment. FIG. 7B shows mice receiving chTNT-3/R38W protein (20-50 μg) as compared to no treatment.

FIG. 9 shows the amino acid sequence of full length native human IL-2 (SEQ ID NO:3).

DETAILED DESCRIPTION OF THE INVENTION

In accordance with the present invention, there is provided a method for identifying IL-2 mutants with reduced toxicity, said method comprising assaying IL-2 mutants comprising a mutation in the permeability enhancing peptide region of IL-2 for vasopermeability activity and for binding affinity for an IL-2 receptor, said mutants with reduced toxicity characterized by substantially reduced vasopermeability and similar binding affinity for an IL-2 receptor as compared to a wildtype form of the IL-2 mutant. In one embodiment, the mutation comprises a substitution in at least one non-wildtype amino acids residue located in the permeability enhancing peptide region of IL-2.

As shown in FIG. 9, mature, native human IL-2 has a 133 amino acid sequence. As used herein, the permeability enhancing peptide region for human IL-2 represents residues 22 to 58 (see U.S. Pat. No. 6,008,319).

Figure 1:
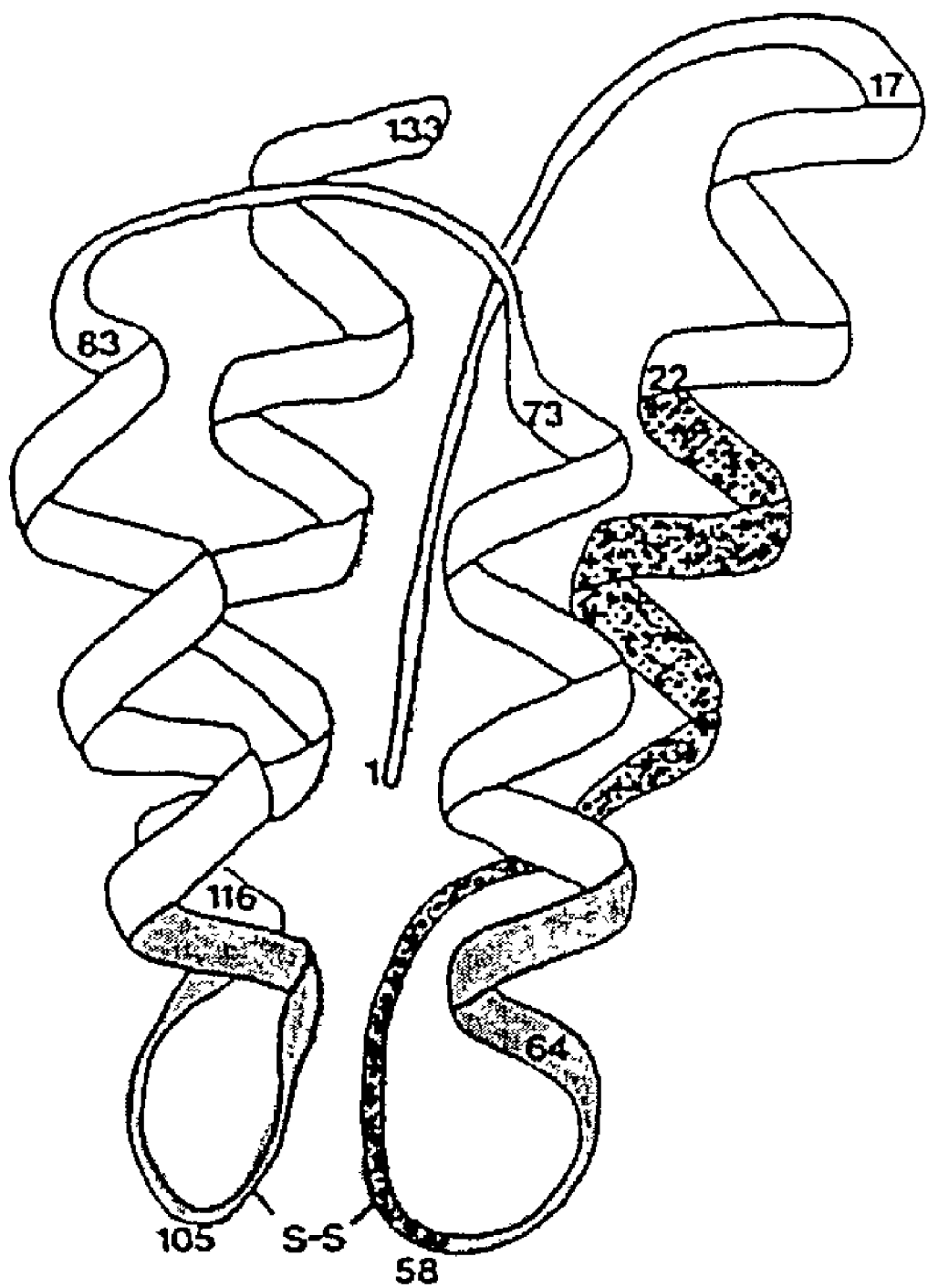
FIG. 1 is a schematic of the IL-2 molecule demonstrating the location of the cytokine (shown as solid; approximately amino acids 40-70, and at approximately amino acids 90-116) and vasopermeability (shown as stippled; amino acids 22-58) activities.

Vasopermeability activity as seen in FIG. 1 maps to a region of the IL-2 that partly overlaps the amino acids believed to be responsible for IL-2's cytokine activity (residues 40-70 and 90-116) (LeBerthon et al., Cancer Res. 51:2694, 1991; Cotran et al., J. Immunol. 140:1883, 1988). Mutations in the vasopermeability region of IL-2 that are outside of the cytokine region of IL-2, specifically residues 22-39, are preferred. Other segments of the vasopermeability enhancing peptide region of IL-2 that are suitable for mutation as disclosed herein include 33 to 58, 37 to 58, or 37 to 72.

A substantial reduction in vasopermeability is achieved when the IL-2 mutant induces less than approximately 75% of the vasopermeability activity of a wildtype form of the IL-2 mutant. IL-2 mutants of the invention may induce less than about 50% and even less than about 25% of such vasopermeability activity.

As used herein, a "wildtype form of the IL-2 mutant" is a form of IL-2 that is otherwise the same as the IL-2 mutant except that the wildtype form has a wildtype IL-2 amino acid at each amino acid position of the IL-2 mutant. For example, if the IL-2 mutant is the full-length IL-2 (i.e., IL-2 not fused or conjugated to any other molecule), the wildtype form of this IL-2 mutant is full length native IL-2. If the IL-2 mutant is a fusion between IL-2 and another polypeptide encoded downstream of IL-2 (e.g., and antibody chain), the wildtype form of this IL-2 mutant is IL-2 with a wildtype amino acid sequence fused to the same downstream polypeptide. Furthermore, if the IL-2 mutant is a truncated form of IL-2 (the mutated or modified sequence within the non-truncated portion of IL-2), then the wildtype form of this IL-2 mutant is a similarly truncated IL-2 that has a wild type sequence.

The ability of an IL-2 mutant to substantially decrease vasopermeability can be examined in a pretreatment vasopermeability animal model. In general, the IL-2 mutant (or the suitable wildtype form of IL-2 mutant) is administered to a suitable animal and, at a later time, the animal is injected i.v. with a vascular leak reporter molecule whose dissemination from the vasculature reflects the extent of vascular permeability. The vascular leak reporter molecule is preferably large enough to reveal permeability with the wildtype form of the IL-2 used for pretreatment. An example of a vascular leak reporter molecule can be a serum protein such as albumin or an immunoglobulin. The vascular leak reporter molecule preferably is detectably labeled such as with a radioisotope to facilitate quantitative determination of the molecule's tissue distribution. Vascular permeability may be measured for vessels present in any of a variety of internal body organs such as liver, lung, and the like, as well as a tumor, including a tumor that is xenografted. Lung is a preferred organ for measuring vaospermeability of full-length IL-2 mutants.

The Examples appended herewith provide a suitable vasopermeability assay for testing IL-2 mutants of the invention, particularly where IL-2 is linked to an antibody polypeptide or antibody molecule. In this model, mice xenografted with LS174T human colon adenocarcinoma cells that form a growing solid tumor are pretreated with the mutant IL-2 fused to the DNA targeting antibody TNT-3 that has targeting activity for human tumor cells. The animals are later administered $^{125}$I-labeled B72.3 monoclonal antibody (a vascular leak reporter molecule), which recognizes the tumor associated glycoprotein-72 (TAG72) on the LS174T tumor cells. Following injection, the percent of the dose of antibody per gram of tumor is determined and compared to pretreatment with native IL-2 fused to the same antibody. Results are expressed as the percent of tumor uptake of B72.3 per gram of tumor in native IL-2 versus mutant forms of IL-2 (see, e.g., summary in Table 5). A decrease in general vasopermeability indicated by a decrease in the percentage dose per gram tumor uptake signifies a potential for a reduced toxicity of the IL-2 mutant (such potential being fully realized in conjunction with the IL-2 mutant's immune activating properties).

IL-2 mutants which maintain substantially similar affinity for IL-2 receptors as compared to a wildtype form of the IL-2 mutant are preferred. Substantially similar binding to the IL-2 receptor is achieved when the IL-2 mutant exhibits greater than approximately 75% of the affinity of the wildtype form of IL-2 mutant for at least one form of the IL-2 receptor. IL-2 mutants that exhibit no more than about 50% of the receptor binding activity compared to a wildtype form of the IL-2 mutant may be useful for particular clinical applications.

The affinity of the mutant IL-2 for various forms of the IL-2 receptor (see Theze et al., *Immunol Today*, 17:481-486, 1996) can be determined in accordance with well established methods. Binding affinity for the low-affinity IL-2 receptor (α; p55) and binding to the intermediate-affinity IL-2 receptor (γ; p70, p75) can be determined in accordance with the method set forth in the Examples using MT-1 and YT-2C2 cell lines, respectively. Binding affinity of IL-2 mutants for high-affinity IL-2 receptor (α γ; p55, p70, p75), may be evaluated using HT-2 cells or other cells known to express this form of the IL-2 receptor. Other forms of the receptor such as the α, αγ and also may be evaluated for affinity to the mutants. Alternatively, affinity can be determined using receptor subunits such as may be obtained by recombinant expression (see e.g., Shanafelt et al., *Nature Biotechnology* 18:1197-1202, 2000). Binding of IL-2 mutants to such receptor subunits and combinations thereof can be determined by standard instrumentation such as a BIAcore instrument (Pharmacia).

The ability of an IL-2 mutant to bind to IL-2 receptors may be indirectly measured by assaying the effects of immune activation that occur downstream of receptor binding. Such assays include IL-2 induced cell proliferation (e.g., proliferation of the IL-2-dependent HT-2 murine T cell lymphoma cells), tumor regression, viral inhibition, immunomodulating activity (e.g., secondary cytokine induction, such as IL-1β, IFN-γ, and TNF-α from human PBMC), lymphokine-activated lymphocyte activity, T cell growth, natural killer cell activity (e.g., measured against Daudi cells), treatment of infections, and the like. A variety of methods are well known in the art for determining these immunological activities of IL-2. Also, details for many of these methods are disclosed in the Examples.

The term "IL-2 mutant" or "mutant IL-2" as used herein is intended to encompass any mutant forms of various forms of the IL-2 molecule including full length IL-2, truncated forms of IL-2 and forms where IL-2 is linked to another molecule such as by fusion or chemical conjugation. "Full-length" when used in reference to IL-2 is intended to mean the natural length IL-2 molecule. For example, full length human IL-2 refers to a molecule that has 133 amino acids (see FIG. 9). These various forms of IL-2 mutants are characterized in having a mutation affecting at least one amino acid position in the permeability enhancing peptide region of IL-2. This mutation may involve substitution, deletion, truncation or modification of the wildtype amino acid residue normally located at that position. Mutants obtained by amino acid substitution are preferred. Unless otherwise indicated, an IL-2 mutant may be referred to herein as an IL-2 mutant peptide sequence, an IL-2 mutant polypeptide, IL-2 mutant protein or IL-2 mutant analog.

A single IL-2 mutant or a mixture of IL-2 mutants may be assayed as described to identify low toxicity mutants. Such mixtures of mutants may include a library of mutants that may be randomized or partially randomized at one or more amino acid positions. Mutant libraries can be prepared by randomizing nucleotides or codons if recombinant expression of IL-2 is contemplated or by randomizing animo acids if synthetic IL-2 is contemplated. Methods for preparing such mutant libraries are well known in the art (see, e.g., Ladner, U.S. Pat. No. 5,837,500; Shatz et al., U.S. Pat. No. 5,498,530; Huse et al. *Science* 246:1275-1281, 1989; and Lam et al., *Nature* 354:82-84, 1991).

The present invention also provides IL-2 mutants characterized by substantially reduced vasopermeability activity and substantially similar binding affinity for an IL-2 receptor compared to a wildtype form of the IL-2 mutant. Such IL-2 mutants comprise at least one mutation in the permeability enhancing peptide region of the IL-2 molecule, the mutation preferably involving substitution of one or more wildtype amino acid residue in that region. Designation of various forms of IL-2 herein is made with respect to the sequence shown and numbered as in FIG. 9, noting only modifications thereof at the subscripted positions. Various designations may be used herein to indicate the same mutation. For example, a mutation from arginine at position 38 to tryptophan can be indicated as $W_{38}$, W38, 38W or R38W.

IL-2 mutants with decreased vasopermeability may be mutated by substitution at amino acid 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 or combinations thereof. In a more preferred embodiment, the IL-2 mutant has a mutation at amino acid 38, 39, 42, or 55, wherein said non-wildtype residue at position 38 is not alanine or glutamine while said non-wildtype residue at position 42 is not lysine. In an even more preferred embodiment, the IL-2 mutant is $W_{38}$, $G_{38}$, $Y_{38}$, $L_{39}$, $K_{42}$ and $Y_{55}$. These mutants exhibit substantially similar binding affinity to low-affinity and intermediate-affinity IL-2 receptors and have substantially reduced vasopermeability activity as compared to a wildtype form of the IL-2 mutant.

Preferable mutations may actually display increased binding affinity for the low- and intermediate-affinity IL-2 receptors. Other characteristics of useful mutants may include the ability to induce proliferation of IL-2 receptor bearing T cells, a reduced ability to induce elaboration of secondary cytokines by peripheral blood mononuclear cells, particularly IL-1β and TNF-α, and a reduced toxicity profile in vivo. Mutants 38G and 55Y, which exhibit substantially reduced vasopermeability activity, but which substantially retain the ability to generate IFN-γ as a secondary cytokine also represent IL-2 mutants of the invention. A particularly preferred IL-2 mutant polypeptide is 38W, which exhibits substantially reduced vasopermeability, retains substantial affinity for the low- and intermediate-affinity IL-2 receptor, and retains 50% or more of the IL-2 dependent cell line HT-2 proliferative activity of native IL-2 (Table 3).

IL-2 mutants of the invention, in addition to having a mutation in the vasopermeability region of IL-2, also may have one or more mutations in the amino acid sequence outside this region. Mutations in human IL-2 affecting position 1-21 and 59-133 can provide additional advantages such as increased expression or stability. For example, the cysteine at position 125 may be replaced with a neutral amino acid such as serine, alanine, threonine or valine, yielding $S_{125}$IL-2, $A_{125}$IL-2, $T_{125}$IL-2 or $V_{125}$IL-2 respectively, as described in U.S. Pat. No. 4,518,584 (RE 33,653). As described therein, one may also delete the N-terminal alanine residue of IL-2 yielding such mutants as des-$A_1S_{125}$ or des-$A_1A_{125}$. A cysteine residue may be substituted for any non-cysteine residue at positions 1-20 and particularly at position 3 as described in U.S. Pat. No. 5,206,344. Alternatively or conjunctively, the IL-2 mutant include mutation whereby methionine normally occurring at position 104 of wild-type IL-2 is replaced by a neutral amino acid such as alanine (see U.S. Pat. No. 5,206,344). The resulting mutants, e.g., des-$A_1A_{104}$ IL-2, des-$A_1A_{104}S_{125}$ IL-2, $A_{104}$IL-2, $A_{104}A_{125}$IL-2, des-$A_1A_{104}A_{125}$IL-2, or $A_{104}S_{125}$IL-2 may be used to conjunction with the preferred IL-2 mutations of the invention that substantially reduced vasopermeability activity while retaining substantially similar binding affinity for an IL-2 receptor compared to a wildtype form of the IL-2 mutant. Also, a threonine at position 3 of the native molecule can be replaced by cysteine to yield e.g., des-$A_1C_3A_{104}$IL-2, des-$A_1C_3A_{104}$ $S_{125}$IL-2, $C_3A_{104}$IL-2, $C_3A_{104}$ $A_{125}$IL-2, des-$A_1C_3A_{104}$ $A_{125}$IL-2, or $C_3A_{104}$ $S_{125}$IL-2, each of which may be used to conjunction with the preferred IL-2 mutations of the invention. In these mutants substitution removes the glycosylation site at position 3 without eliminating biological activity (see Japanese Patent Application No. 235,638 filed Dec. 13, 1983). These and other mutants may be found in U.S. Pat. No. 5,116,943 (see claim 5) and in Weiger et al., Eur. J. Biochem., 180:295-300 (1989).

Mutations of the invention that substantially reduce vasopermeability activity while retaining substantially similar binding affinity for an IL-2 receptor compared to a wildtype form of the IL-2 mutant also may be combined with other toxicity reducing mutations such as when asparagine at position 88 is replaced by arginine (i.e., $R_{88}$IL-2, also known as BAY 50-4798), described by Shanafelt et al., Nature Biotech. 18:1197-1202 (2000). As shown in the Examples, the N88R mutant has reduced toxicity but this does not occur by reduced vasopermeability. According to Shanafelt et al., reduced toxicity for this mutant results from decreased binding to the intermediate affinity (NK) IL-2 receptor. Thus, an IL-2 mutant that contains both a vasopermeability reducing mutation in the vasopermeability enhancing peptide region of IL-2 as well as the N88R mutation that reduces toxicity by reducing binding to the intermediate IL-2 receptor will provide an IL-2 mutant with unique and useful therapeutic efficacy.

IL-2 mutants of the invention can be prepared by deletion, substitution, insertion or modification using genetic or chemical methods well known in the art. Genetic methods may include site-directed mutagenesis, PCR, gene synthesis, and the like. In this regard, the nucleotide sequence of native IL-2 has been described by Taniguchi et al. (Nature 302:305, 1983) and nucleic acid encoding human IL-2 is available from public depositories such as the American Type Culture Collection (Rockville Md.). Substitution or insertion may involve natural as well as non-natural amino acid residues. Amino acid modification includes well known methods of chemical modification such as the addition of glycosylation sites or carbohydrate attachments, and the like.

Mutant IL-2 may be prepared by recombinant expression methods such as in bacteria and yeast as described previously (see U.S. Pat. No. 5,116,943). In general, nucleic acid encoding the mutant IL-2 can be cloned into an expression vector for high yield expression of the encoded product. The expression vector can be part of a plasmid, virus, or may be a nucleic acid fragment. The expression vector includes an expression cassette into which the nucleic acid encoding the IL-2 mutant is cloned in operable association with a promoter. The expression cassette may also include other features such as an origin of replication, and/or chromosome integration elements such as retroviral LTRs, or adeno associated viral (AAV) ITRs. If secretion of the IL-2 mutant is desired, DNA encoding a signal sequence may be placed upstream of the nucleic acid encoding the mature amino acids of the mutant IL-2. DNA encoding a short protein sequence that could be used to facilitate later purification (e.g., a histidine tag) or assist in labeling the IL-2 mutant may be included within or at the ends of the IL-2 mutant encoding nucleic acid. The expression vector pEE12/chTNT-3 HC/huIL-2 (mutant or native) described in the Examples and which encodes a fusion protein comprising human IL-2 (mutant or native) coupled to the carboxy-terminus of chTNT-3 heavy chain via a non-cleavable seven amino acid linker is one example of a useful expression vector.

Cells suitable for replicating and for supporting expression of IL-2 mutants are well known in the art. Such cells may be transfected or transduced as appropriate with the particular expression vector and large quantities of vector containing cells can be grown for seeding large scale fermenters to obtain sufficient quantities of the IL-2 mutant for clinical applications. Such cells may include prokaryotic microorganisms, such as E. coli, or various other eukaryotic cells, such as Chinese hamster ovary cells (CHO), insect cells, or the like. Standard technologies are known in the art to express foreign genes in these systems. For example, the NSO murine myeloma cell line, which was transfected with expression vector pEE12/chTNT-3 HC/huIL-2 (mutant or native) as described in the Examples, is suitable for supporting expression of an antibody mutant IL-2 fusion protein.

An IL-2 mutant can be prepared where the IL-2 polypeptide segment is linked to one or more molecules such as a polypeptide, protein, carbohydrate, lipid, nucleic acid, polynucleotide or molecules that are combinations of these molecules (e.g., glycoproteins, glycolipids etc). The IL-2 mutant also may be linked to organic moiety, inorganic moiety or pharmaceutical drug. As used herein, a pharmaceutical drug is an organic containing compound of about 5,000 daltons or less.

The IL-2 mutant may also be linked to multiple molecules of the same type or to more than one type of molecule. In some cases, the molecule that is linked to IL-2 can confer the ability to target the IL-2 to specific tissues or cells in an animal. In this embodiment, the other molecule may have affinity for a ligand or receptor in the target tissue or cell, thereby directing the IL-2 to the target tissue or cell. Targeting molecules include, for example, antibodies specific for cell surface or intracellular proteins, ligands of biological receptors, and the like. Such antibodies may be specific for well known tumor associated antigens such as carcinoembryonic antigen, the TAG-72 antigen, the EGF receptor, and the like. Antibodies to DNA such as the TNT antibody described in the Examples is an example of a useful targeting molecule that can be fused or conjugated to mutant IL-2.

The IL-2 mutant also may be linked to any biological agent including therapeutic compounds such as anti-neoplastic agents include paclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin, and the like. Anti-microbial agents include aminoglycosides including gentamicin, antiviral compounds such as rifampicin, 3'-azido-3'-deoxythymidine (AZT) and acylovir, antifungal agents such as azoles including fluconazole, plyre macrolides such as amphotericin B, and candicidin, anti-parasitic compounds such as antimonials, and the like. Hormones may include toxin such as diphtheria toxin, cytokine such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, hormone receptors such as the estrogen receptor. Also included are non-steroidal anti-inflammatories such as indomethacin, salicylic acid acetate, ibuprofen, sulindac, piroxicam, and naproxen, and anesthetics or analgesics. Also included are radioisotopes such as those useful for imaging as well as for therapy.

Figure 2:
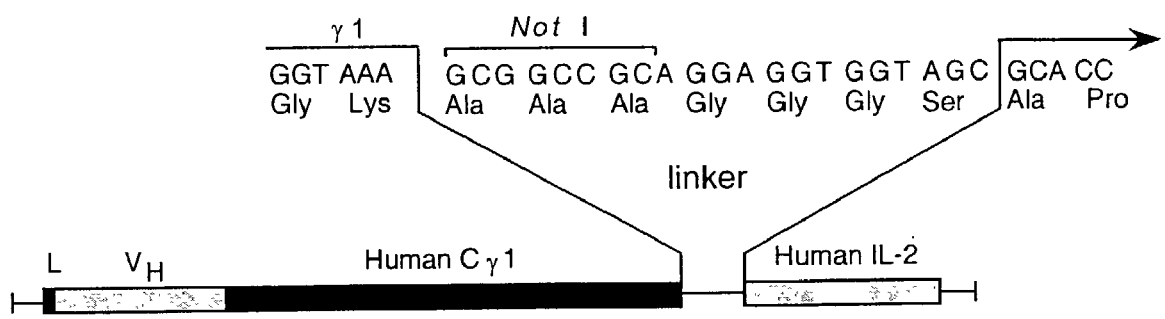
FIG. 2 is a schematic showing the nucleotide sequence (SEQ ID NO:1) and amino acid sequence (SEQ ID NO:2) of a linker within the bordering sequence of human IgG1 heavy chain and human IL-2 that make up a chimeric antibody (chTNT-3 heavy chain)/IL-2 fusion protein).

An IL-2 mutant which is a fusion between IL-2 and another polypeptide can be designed such that the IL-2 sequence is fused directly to the polypeptide or indirectly through a linker sequence. The composition and length of the linker may be determined in accordance with methods well known in the art and may be tested for efficacy. An example of a linker sequence between IL-2 and an antibody heavy chain is shown in FIG. 2. Additional sequences may also be included to incorporate a cleavage site to separate the individual components of the fusion if desired, for example an endopeptidase recognition sequence. In addition, an IL-2 mutant may also be synthesized chemically using methods of polypeptide synthesis as is well known in the art (e.g., Merrifield solid phase synthesis).

As used herein, "antibody" is intended to include all forms of an antibody, including all natural and unnatural antibody forms. This includes the typical antibody that consists of four subunits including two heavy chains and two light chains, domain-deleted antibodies, Fab fragments, Fab'2 fragments, Fv fragments, single chain Fv antibodies, and the like. An antibody also includes the heavy chain alone or the light chain alone. Methods to produce polyclonal antibodies and monoclonal antibodies are well known in the art (see, e.g., Harlow and Lane, "Antibodies, a laboratory manual." Cold Spring Harbor Laboratory, 1988). Non-naturally occurring antibodies can be constructed using solid phase peptide synthesis, can be produced recombinantly or can be obtained, for example, by screening combinatorial libraries comprising variable heavy chains and variable light chains (see, e.g., U.S. Pat. No. 5,969,108 to McCafferty).

IL-2 may be genetically fused to single polypeptide antibody forms or may be chemically conjugated to any of the antibody forms. Fusion of IL-2 to an antibody heavy chain is described in the Examples. Any animal species of antibody can be linked to a mutant IL-2. If the mutant IL-2/antibody conjugate or fusion is intended for human use, a chimeric form of the antibody may be used wherein the constant regions of the antibody are from a human. A fully humanized form of the antibody can also be prepared in accordance with methods well known in the art (see, e.g., U.S. Pat. No. 5,565,332 to Winter). Cells expressing a mutant-IL-2 fused to either the heavy or the light antibody chain may be engineered so as to also express the other of the antibody chains such that the expressed mutant IL-2 fusion product is an antibody that has both a heavy and a light chain.

Mutant IL-2 may be chemically conjugated to another molecule using well known chemical conjugation methods. Bi-functional cross-linking reagents such as homofunctional and heterofunctional cross-linking reagents well known in the art can be used for this purpose. The type of cross-linking reagent to use depends on the nature of the molecule to be coupled to IL-2 and can readily be identified by those skilled in the art. Alternatively, or in addition, mutant IL-2 and/or the molecule to which it is intended to be conjugated may be chemically derivatized such that the two can be conjugated in a separate reaction as is also well known in the art.

Figure 3:
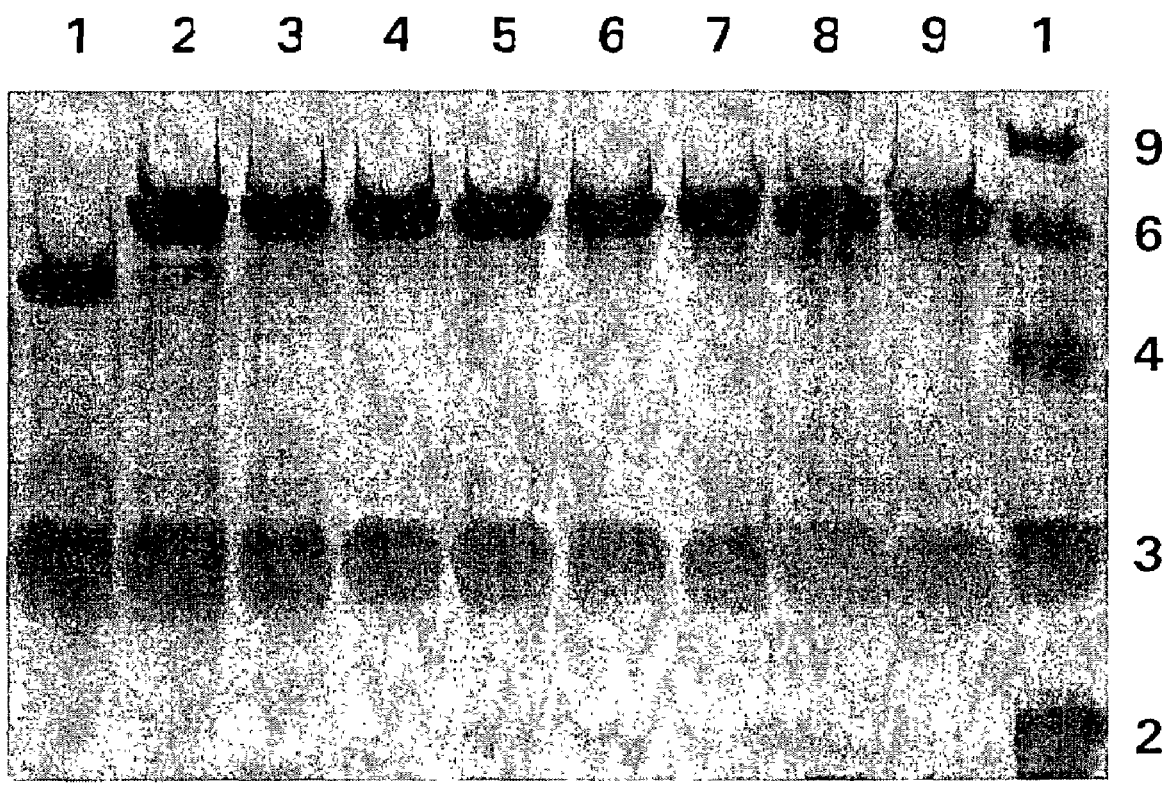
FIG. 3 shows SDS-PAGE analysis (10% polyacrylamide tris-glycine reduced gel) of chTNT-3 antibody, chTNT-3/ native IL-2 fusion protein and chTNT-3/IL-2 mutant fusion proteins. The gel was stained with Coomassie Blue. Samples are as follows: biotinylated chTNT-3 (lane 1), chTNT-3/IL-2 (lane 2), chTNT-3/D20K (lane 3), chTNT-3/R38G(lane 4), chTNT-3/R38W (lane 5), chTNT-3/M39V (lane 6), chTNT-3/M39L (lane 7), chTNT-3/F42K (lane 8), chTNT-3/H55Y (lane 9), and molecular weight markers (lane 10).
Figure 4A:
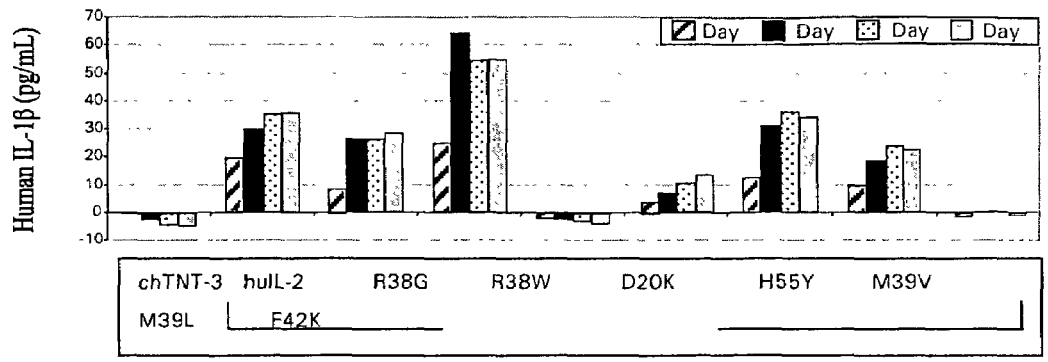
FIGS. 4A-4C profile secondary cytokine secretion by stimulated peripheral blood mononuclear cells (PBMC) incubated with chTNT-3 antibody, chTNT-3/native IL-2, or chTNT-3/IL-2 mutant fusion proteins in serum free media. Cytokine levels representative for the two PBMC donors were determined by indirect ELISA of culture media for the days of culture indicated.
Figure 4B:
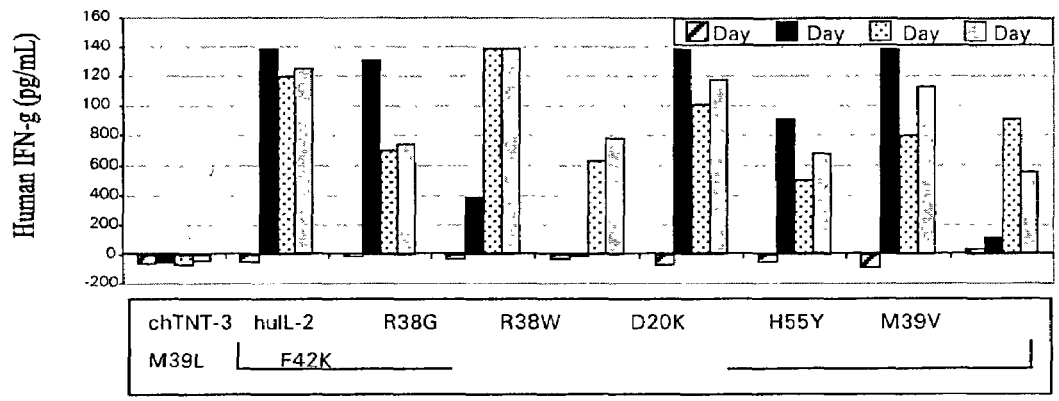
Figure 4C:
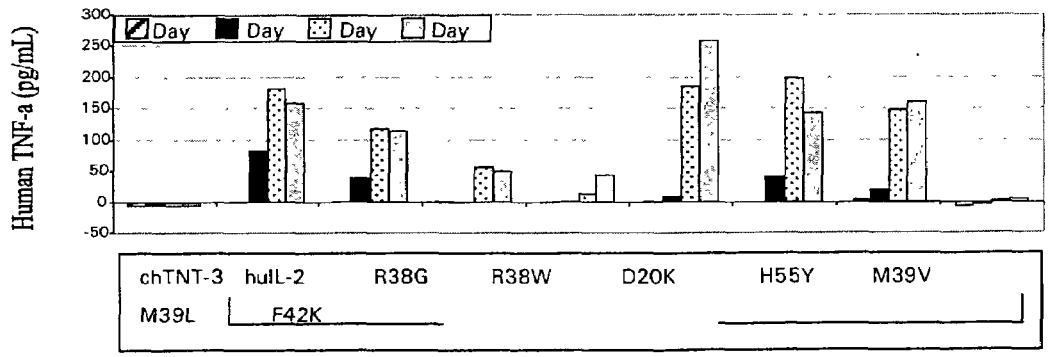
Figure 5A:
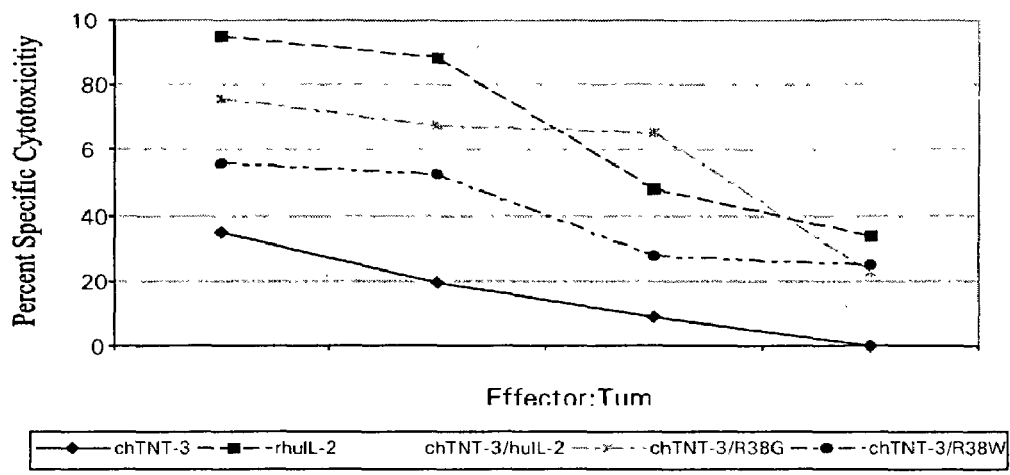
FIGS. 5A-5C depict lymphokine-activated killer (LAK) cell activity generated by activation of PBMC with chTNT-3 antibody alone, recombinant human IL-2 alone (rhuIL-2), chTNT-3/native IL-2 fusion protein, or chTNT-3/IL-2 mutant fusion proteins. LAK activity was determined by four hour cytotoxicity activity against Daudi lymphoma cells.
Figure 5B:
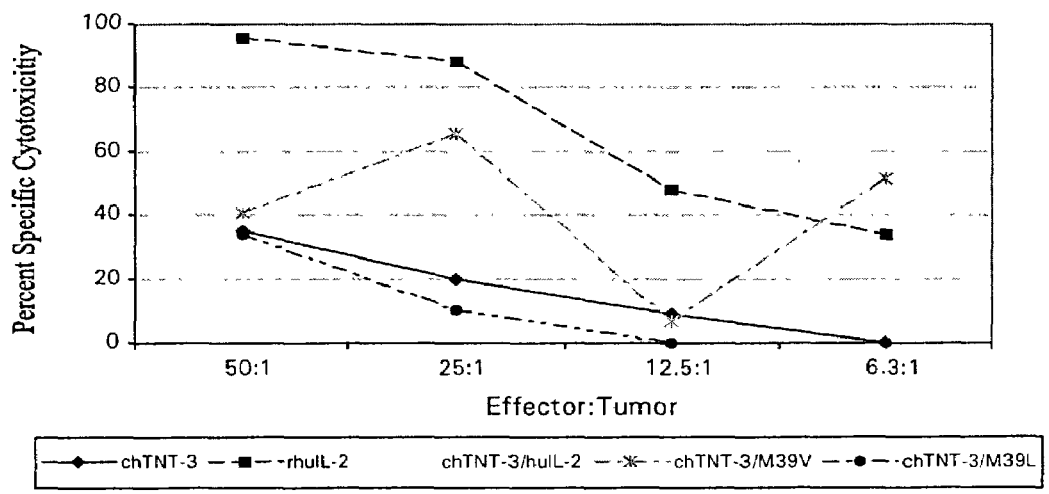
Figure 5C:
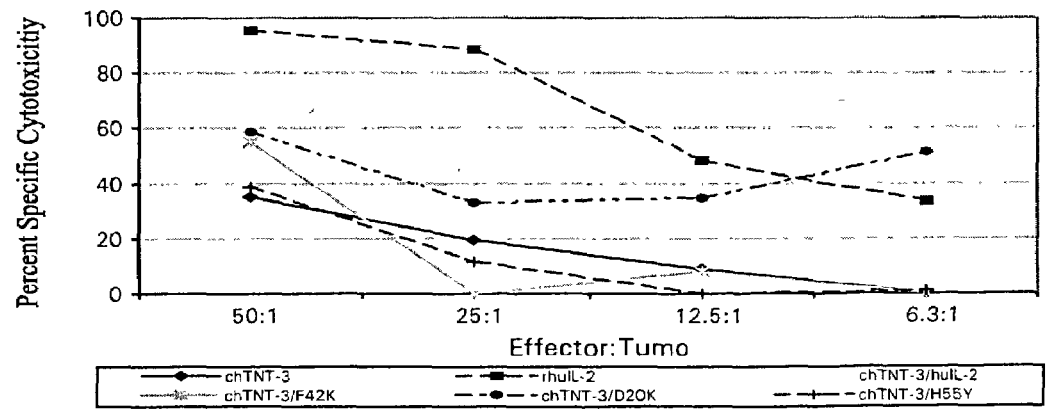

IL-2 mutants prepared as described herein may be purified by biochemical methods well known in the art. Such methods may include affinity chromatography such as binding and elution to a ligand or antigen to which the fusion protein is reactive. For example, sequential Protein A affinity chromatography, and ion-exchange chromatography can be used to isolate a fusion protein (or conjugate) essentially as described in the Examples. The purity of the mutant IL-2 fusion protein can be determined by any of a variety of well known analytical methods including gel electrophoresis, high pressure liquid chromatography, and the like. For example, the chimeric heavy chain fusion proteins expressed as described in the Examples were shown to be intact and properly assembled as demonstrated by reducing SDS-PAGE (FIG. 3). Two bands were resolved for chTNT-3/huIL-2 at approximately $M_r$ 25,000 and $M_r$ 70,000, corresponding to the predicted molecular weights of the immunoglobulin light chain and heavy chain/IL-2 fusion protein.

Further chemical modification of the IL-2 mutant polypeptide may be desirable. For example, problems of immunogenicity and short half-life may be improved by conjugation to substantially straight chain polymers such as polyethylene glycol (PEG) or polypropylene glycol (PPG) (see, e.g., PCT WO87/00056).

In accordance with another aspect of the present invention, there is provided a method for stimulating the immune system of an animal by administering the IL-2 mutants of the invention. The method is useful to treat disease states where the host immune response is deficient. In treating a subject, a therapeutically effective dose of compound (i.e., active ingredient) is administered. A therapeutically effective dose refers to that amount of the active ingredient that produces amelioration of symptoms or a prolongation of survival of a subject. An effective dose will vary with the characteristics of the IL-2 mutant to be administered, the physical characteristics of the subject to be treated, the nature of the disease or condition, and the like. A single administration can range from about 50,000 IU/kg to about 1,000,000 IU/kg or more, more typically about 600,000 IU/kg. This may be repeated several times a day (e.g., 2-3×), for several days (e.g., about 3-5 consecutive days) and then may be repeated one or more times following a period of rest (e.g., about 7-14 days). Thus, an effective dose may comprise only a single administration or many administrations over a period of time (e.g., about 20-30 individual administrations of about 600,000 IU/kg each given over about a 10-20 day period).

Disease states for which the mutant IL-2 can be administered comprise, for example, a tumor or infection where a cellular immune response would be a critical mechanism for specific immunity. Stimulation of the immune system may include any one or more of a general increase in immune function, an increase in T cell function, a restoration of lymphocyte function, an increase in the expression of IL-2 receptors, an increase in T cell responsiveness, an increase in natural killer cell activity or lymphokine-activated killer cell activity, and the like. Illustrative of specific disease states for which IL-2 mutants of the present invention can be employed include cancer, specifically renal cell carcinoma or melanoma; immune deficiency, specifically in HIV-positive patients, immunosuppresed patients, and autoimmune disorders, chronic infection and the like.

The IL-2 mutant may be administered in combination with one or more therapeutic agents, for example, a cytokine, antiviral or antifungal agent. The term "therapeutic agent" encompasses any agent administered to treat a symptom or disease in an animal in need of such treatment. The IL-2 mutant may also be administered as a component of a vaccine, i.e. combined with essentially any preparation intended for active immunological prophylaxis.

Toxicity and therapeutic efficacy of an IL-2 mutant can be determined by standard pharmaceutical procedures in cell culture or experimental animals (see, e.g. Example 3B). Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. IL-2 mutants that exhibit large therapeutic indices are preferred. The data obtained from these cell culture assays and animal studies can be used in formulating a range of dosages suitable for use in humans. The dosage of such mutants lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition.

The attending physician for patients treated with IL-2 mutants would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

IL-2 mutants of the invention may be administered to an individual alone as a pharmaceutical preparation appropriately formulated for the route of delivery and for the condition being treated. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and the like. For transmucosal administration, penetrants appropriate to the barrier to be permeated are used in the formulation. Such penetrants are generally known in the art.

IL-2 mutants may be manufactured as a formulation with one or more pharmaceutically acceptable carriers or excipient(s) as is well known in the art. Techniques for formulation and administration may be found in "Remington's Pharmaceutical Sciences," (18th ed., Mack Publishing Co., Easton, Pa., 1990). Specific examples of IL-2 formulations are described in U.S. Pat. Nos. 4,604,377 and 4,766,106. The IL-2 mutant may be formulated as a liquid with carriers that may include a buffer and or salt such as phosphate buffered saline. Alternatively, the IL-2 mutant may be formulated as a solid with carriers or fillers such as lactose, binders such as starches, and/or lubricants such as talc or magnesium stearate and, optionally, stabilizers.

For oral delivery, the formulated end product may be a tablet, pill, capsule, dragee, liquid, gel, syrup, slurry, suspension, and the like. Also, push-fit capsules made of gelatin, as well as soft, sealed capsules made of gelatin and a plasticizer, such as glycerol or sorbitol may be used. The push-fit capsules can contain the active ingredients in admixture with fillers as above while in soft capsules, the active compounds may be dissolved or suspended in suitable liquids, such as fatty oils, liquid paraffin, or liquid polyethylene glycols.

Formulation for oral delivery may involve conventional mixing, dissolving, granulating, dragee-making, levigating, emulsifying, encapsulating, entrapping, lyophilizing processes, and the like. The IL-2 mutant also may be mixed with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, sorbitol, and the like; cellulose preparations such as, for example, maize starch, wheat starch, rice starch, potato starch, gelatin, gum tragacanth, methyl cellulose, hydroxypropylmethylcellulose, sodium carboxymethylcellulose, polyvinylpyrrolidone (PVP), and the like, as well as mixtures of any two or more thereof. If desired, disintegrating agents may be added, such as cross-linked polyvinyl pyrrolidone, agar, alginic acid or a salt thereof such as sodium alginate, and the like.

If injection is desired, the IL-2 mutant may be formulated in aqueous solutions, preferably in physiologically compatible buffers such as Hank's solution, Ringer's solution, or physiological saline buffer. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

The present invention also provides a method of producing a low toxicity IL-2 in a form suitable for administration in vivo, said method comprising:

a) obtaining a mutant IL-2 characterized by substantially reduced vasopermeability activity and substantially similar binding affinity for an IL-2 receptor compared to a wildtype form of the IL-2 mutant; and b) formulating the mutant IL-2 with at least one pharmaceutically acceptable carrier, whereby a preparation of low toxicity IL-2 is formulated for administration in vivo. In this aspect, the mutant IL-2 may be obtained by culturing a recombinant organism containing nucleic acid encoding the mutant IL-2 or by producing the mutant IL-2 by in vitro chemical synthesis.

The invention will now be described in greater detail by reference to the following non-limiting examples.

EXAMPLES

Example 1

Reagents

This example provides the preferred reagents for practice of the embodied invention. One skilled in the art can readily appreciate comparable materials that can be substituted in place of these reagents.

The Glutamine Synthase Gene Amplification System, including the expression plasmids pEE6/hCMV-B and pEE12 as well as the NSO murine myeloma expression cell line, were purchased from Lonza Biologics (Slough, UK). Restriction endonucleases, T4 DNA ligase, Vent polymerase, and other molecular biology reagents were purchased from either New England Biolabs (Beverly, Mass.) or Boehringer Mannheim (Indianapolis, Ind.). Dialysed fetal bovine serum, crude DNA from salmon testes, single-stranded DNA from calf thymus, chloramine T, and 2,2'-azino-bis(3-ethylbenzthiazoline-6-sulfonic acid) diammonium salt (ABTS) were purchased from Sigma Chemical Co. (St. Louis, Mo.). Recombinant human interleukin-2 was purchased from Chiron (Emeryville, Calif.). The Griess Reagent System, containing sulfanilamide solution, N-1-naphthylethylenediamine dihydrochloride solution, and nitrite standards, was purchased from the Promega Corporation (Madison, Wis.). $^{125}$I was obtained from DuPont New England Nuclear (North Billerica, Mass.) as sodium iodide in 0.1 N sodium hydroxide. BALB/c mice were obtained from Harlan Sprague-Dawley (Indianapolis, Ind.). Sulfosuccinimidyl 6-(biotinamido) hexanoate (Sulfo-NHS-LC biotin) was purchased from Pierce (Rockford, Ill.). HRPO-conjugated secondary reagents (goat-anti-human IgG (FcSp) and streptavidin) were purchased from CalTag (Burlingame, Calif.).

The Daudi lymphoma cell line (Ohsugi et al., *J. Nat. Cancer Inst.* 65:715. 1980), HT-2 lymphoma line (Shipley et al., *Cell. Immunol.* 93:459, 1985), and LS174T human colorectal carcinoma cell line (Tom et al., *In Vitro* I12:180, 1976) were obtained from the American Type Culture Collection (Manassas, Va.). The Madison 109 murine lung adenocarcinoma (Marks et al., *Cancer Treatment Reports* 61:1459, 1977) was obtained from the National Cancer Institute (Frederick, Md.). The MT-1 human T lymphotropic virus-I-transformed T cell line (Tsudi et al., *J. Immunol.* 143:4039, 1989) and YT-2C2 cell line, a subcdone of the acute lymphoblastic lymphoma cell line YT (Yodoi et al., *J. Immunol.* 134:1623, 1985), were generous gifts of Thomas L. Ciardelli (Dartmouth Medical School).

Example 2

Development and Characterization of IL-2 Mutant Polypeptides

This example provides methods of creating IL-2 mutant polypeptides and chimeric antibody/IL-2 fusion proteins (mutant or native). In addition, this example provides methods for determining the cytokine function and binding properties of resultant IL-2 molecules in vitro.

A. Construction and Expression of IL-2 and Antibody/IL-2 Fusion Proteins. The construction of the chimeric monoclonal antibody TNT-3 (chTNT-3, IgG$_1$, κ) and the fusion protein of this antibody with IL-2 have been previously described (Hornick et al., *Cancer Biotherapy & Radiopharmaceuticals* 13:255, 1998; Hornick et al., *J. Nucl. Med.* 41:355, 2000).

IL-2 mutant cDNA was prepared by site-directed mutagenesis to mutate amino acid 20 from aspartic acid to lysine (D20K), amino acid 38 from arginine to glycine (R38G) or tryptophan (R38W), amino acid 39 from methionine to valine (M39V) or leucine (M39L), amino acid 42 from phenylalanine to lysine (F42K), and amino acid 55 from histidine to tyrosine (H55Y) using the following 5' and 3' primer pairs, respectively:

```
                                    (SEQ ID NO.4)
  D20K-5'-TTACTGCTGA AATTACAGA TG-3',
  and
                                    (SEQ ID NO.5)
  5'-CATCTGTAAT TTCAGCAGTA A-3';

(SEQ ID NO.6)
  R38G/W-5'-AAACTCACC(G/T) GGATGCTCAC A-3',
  and
                                    (SEQ ID NO.7)
  5'-TGTGAGCATC C(A/C)GGTGAGTT T-3';

(SEQ ID NO.8)
  M39V/L-5'-CTCACCAGG(G/C) TGCTCACATT T-3',
  and
                                    (SEQ ID NO.9)
  5'-AAATGTGAGC A(G/C)CCTGGTGA G-3';

(SEQ ID NO.10)
  F42K-5'-ATGCTCACAA AGAAGTTTTA C-3',
  and
                                    (SEQ ID NO.11)
  5'-GTAAAACTTC TTTGTGAGCA T-3';

(SEQ ID NO.12)
  H55Y-5'-GAACTGAAAT AATCTTCAGT GT-3',
  and
                                    (SEQ ID NO.13)
  5'-ACACTGAAGA TATTTCAGTT C-3'.
```

IL-2 mutant cDNA was similarly prepared to mutate amino acid 38 from arginine to tyrosine (R38Y) or to glutamic acid (R38E).

The full-length IL-2 mutant was then amplified by PCR with the following primers:

```
                                    (SEQ ID NO.14)
  5'-GGTAAAGCGG CCGCAGGAGG TGGTAGCGCA CCTACTTCAA
  GTTCTACA -3'; and (SEQ ID NO.15)
  5'-TCATGCGGCC GCTCAAGTTA GTGTTGAGAT GATGCT-3',
``` which appended a NotI restriction site and codons for a polypeptide linker to the 5' end, and a stop codon and NotI site at the 3' end of the IL-2 mutant cDNA.

The resulting PCR product was then restricted with Not I and cloned into the Not I restricted pEE12/chTNT-3 HC expression vector to produce the chTNT-3/IL-2 mutant fusion construct (see FIG. 2). Constructs were introduced in to target cells using standard electroporation techniques. These fusion proteins were expressed from NSO murine myeloma cells for long term stable expression according to the manufacturer's protocol (Lonza Biologics). The highest producing clone was scaled up for incubation in a 3 L stir flask bioreactor and the fusion protein purified from the spent culture medium by sequential Protein A affinity chromatography and ion-exchange chromatography, using methods known in the art. The fusion protein was analyzed by sodium dodecyl sulfate polyacrylamide gel electrophoresis (SDS-PAGE) under reducing conditions and stained with Coomassie blue to demonstrate proper assembly and purity (see FIG. 3).

chTNT-3/IL-2 mutant-secreting clones were initially identified by indirect ELISA analysis of supernatants using microtiter plates coated with crude DNA preparations from calf thymus at 50 µg/mL to detect binding of the TNT antibody portion of the fusion protein. Following this initial screening, production rate assays were performed by incubating $1 \times 10^6$ cells in 1 mL of selective medium for 24 hours, after which the supernatants were analyzed by indirect ELISA analysis using microtiter plates coated with single-stranded DNA preparations from salmon testes at 100 µg/mL. Detection of chTNT-3 and chTNT-3 fusion proteins bound to the DNA antigen was accomplished with horseradish-peroxidase-conjugated goat-anti-human IgG (FcSp) followed by color development produced by enzymatic cleavage of ABTS. Dilutions of chTNT-3 were used to generate a standard curve using a 4-parameter fit by an automated ELISA reader (Bio-Tek Instruments, Winooski, Vt.), from which concentrations of unknowns were estimated and expressed as µg/mL/$10^6$ cells/24 hours.

B. Determination of IL-2 Receptor Binding. The purified antibody/IL-2 fusion proteins were examined for their ability to bind to different forms of the IL-2 receptor using various available cell lines. Table 1 shows the characteristics of IL-2 receptors and expressing cell lines.

TABLE 1

Interleukin-2 Receptors and Native IL-2 Binding Affinity

| Receptor | Protein | Affinity | Cell Line |
| --- | --- | --- | --- |
| Low-Affinity | α (p55) | $K_d = 10^{-8}$M | MT-1 |
| Intermediate-Affinity | βγ (p70, p75 complex) | $K_d = 10^{-9}$M | YT-2C2 |
| High-Affinity | αβγ (p55 and p70, p75 complex) | $K_d = 10^{-11}$M | HT-2 |

Relative binding studies were performed on MT-1 and YT-2C2 cell lines using the method of Frankel and Gerhard (*Mol. Immunol.* 16:101, 1979) to determine the avidity constant of the antibody/IL-2 mutant fusion proteins to the low- and intermediate-affinity IL-2 receptors, respectively. The MT-1 cell line is an HTLV-I-transformed T cell line that lacks IL-2Rβ expression (i.e., only expresses IL-2Rα and γ) (Oda et al., *Intl. Immunol.* 9:1303, 1997). In contrast, the YT-2C2 cell line, a subclone of the acute lymphoblastic lymphoma YT cell line, is an NK-like cell line that lacks IL-2Rα expression and thus only expresses IL-2Rβ and γ (Yodoi et al., *J. Immunol.* 134:1623, 1985; Farner et al., *Blood* 8:4568, 1995).

Cells were harvested and dead cells were removed by Ficoll-Hypaque density centrifugation to remove cells with exposed DNA that could bind to the TNT-3 portion of the antibody/IL-2 fusion protein. The purified viable cells were then used in IL-2 binding studies within one hour of purification. These target cells were incubated with 10 to 100 ng of $^{125}$I-labeled chTNT-3/IL-2 fusion protein or mutant fusion protein in PBS for 30 minutes at room temperature with constant mixing. This short incubation period was chosen to allow sufficient time for the binding and internalization of the IL-2 containing proteins, but insufficient time for the cell to metabolize these proteins. To minimize contribution of the antibody moiety to fusion protein binding to the target cells, a 10-fold molar excess of unlabelled antibody was used to prevent binding of the TNT-3 portion of the fusion protein to the cells. The activity in the supernatants after cell removal was then measured in a gamma counter and the amount of bound radioactivity (cpm) determined by subtractive analysis. The amount of bound fusion protein was then calculated from the cell-bound radioactivity and the specific activity (cpm/ng) of the radiolabeled antibody preparation. Scatchard plot analysis was used to obtain the slope. The equilibrium or avidity constant $K_a$ was calculated by the equation $K_a = -(\text{slope}/n)$, where n is the valence of the fusion protein (2 for IgG fusion protein).

TABLE 2

IL-2 Receptor Binding Affinity of chTNT-3/IL-2 and chTNT-3/IL-2 Mutant Fusion Proteins

| ChTNT-3 Antibody/IL-2 Fusion Protein | * Low-affinity IL-2 Receptor | #Intermediate-affinity IL-2 Receptor |
| --- | --- | --- |
| IL-2 Native | $1.18 \times 10^9$ | $1.18 \times 10^9$ |
| D20K IL-2 Mutant | $1.61 \times 10^9$ | $0.57 \times 10^9$ |
| R38G IL-2 Mutant | $1.35 \times 10^9$ | $1.56 \times 10^9$ |
| R38W IL-2 Mutant | $1.20 \times 10^9$ | $1.63 \times 10^9$ |
| M39V IL-2 Mutant | $1.18 \times 10^9$ | $1.37 \times 10^9$ |
| M39L IL-2 Mutant | $1.02 \times 10^9$ | $1.43 \times 10^9$ |
| F42K IL-2 Mutant | $1.50 \times 10^9$ | $0.90 \times 10^9$ |
| H55Y IL-2 Mutant | $0.90 \times 10^9$ | $1.34 \times 10^9$ |

*Performed using MT-1 cells.
Performed using YT-2C2 cells.

The results of IL-2 receptor binding to the various antibody/IL-2 fusion proteins shown in Table 2 indicate that the majority of antibody/IL-2 mutant fusion proteins demonstrated similar binding profiles with minor variability compared to the native fusion protein. The R38W mutant IL-2/antibody fusion protein displayed increased affinity for both the low- and intermediate-affinity IL-2 receptors. The D20K and F42K mutant IL-2/antibody fusion proteins displayed decreased affinity for the intermediate-affinity IL-2 receptor and an increased affinity to the low-affinity IL-2 receptor relative to the native fusion protein. In contrast, the H55Y mutant IL-2/antibody fusion protein showed reduced affinity to the low-affinity IL-2 receptor with minimal alteration in intermediate-affinity IL-2 receptor binding.

C. Determination of IL-2 Proliferation Activity. The purified antibody/IL-2 fusion proteins were examined for their ability to stimulate proliferation in cell-based assays utilizing the murine IL-2-dependent cell line HT-2 (Buttke et al., *J. Immunol. Meth.* 157:233, 1993; Gieni et al., *J. Immunol. Meth.* 187:85, 1995). Briefly, freshly harvested HT-2 cells were washed three times with sterile PBS to remove residual IL-2. The cells were placed in sterile 96-well flat-bottomed tissue culture plates in duplicate at $1 \times 10^5$ cells/mL with complete RPMI medium or RPMI medium supplemented with a recombinant IL-2 standard (rhu IL-2), chTNT-3, chTNT-3/IL-2 fusion protein or chTNT-3/IL-2 mutant fusion protein, and incubated in a 5% $CO_2$, 37° C. humidified atmosphere. After 72 hours, relative IL-2-dependent cellular proliferation was determined utilizing the CellTiter 96® AQueous One Solution Cell Proliferation Assay (Promega, Madison, Wis.), a one-step colorimetric method that determines the relative conversion of the tetrazolium compound MTS to a colored formazan product. The absorbance of each sample at 490 nm was determined using a Bio-Tek plate reader and the results were graphed to determine the specific activities (IU/mg) of the fusion proteins.

TABLE 3

Relative ability of chTNT-3/IL-2 and chTNT-3/IL-2 mutant fusion proteins stimulate the IL-2 dependent HT-2 cell line.

| ChTNT-3 Antibody/IL-2 Fusion Protein | IL-2 Proliferation Activity (HT-2) |
|---|---|
| ChTNT-3 | − |
| ChTNT-3/IL-2 Native | + + + + |
| ChTNT-3/D20K IL-2 Mutant | − |
| ChTNT-3/38G IL-2 Mutant | + |
| ChTNT-3/R38W IL-2 Mutant | + + + |
| ChTNT-3/R38Y IL-2 Mutant | + + |
| ChTNT-3/R38E IL-2 Mutant | − |
| ChTNT-3/M39V IL-2 Mutant | + |
| ChTNT-3/M39L IL-2 Mutant | + |
| ChTNT-3/F42K IL-2 Mutant | + |
| ChTNT-3/H55Y IL-2 Mutant | + |
| ChTNT-3/N88R IL-2 Mutant | + + + |

Expressed as percent of native IL-2 activity: − = no activity, + = less than 25% activity, + + = 25-50% activity, + + + = 51-75% activity, + + + + = 76-100%.

The results presented in Table 3 show that the majority of the antibody/IL-2 mutant fusion proteins retained their ability to stimulate proliferation of HT-2 cells, with the exception of the D20K and R38E mutant IL-2/antibody fusion proteins. Notably, the R38W mutant IL-2/antibody fusion protein exhibited 51-75% activity in comparison to the native IL-2/antibody fusion protein. It also is noted that the N88R IL-2 mutant showed strong IL-2 proliferative activity, similar in magnitude to that seen for the R38W IL-2 mutant.

D. Quantitation Of Secondary Cytokine Induction. The purified antibody/IL-2 fusion proteins were examined for their ability to induce the expression of the cytokines interleukin-1β (IL-1β), interferon-γ (IFN-γ), and tumor necrosis factor-α (TNF-α) from human peripheral blood mononuclear cells (PBMC) using indirect ELISA analysis. Freshly purified human PBMC were isolated from healthy normal donors by leukopheresis and fractionated on Histopaque 1077 (Sigma-Aldrich, St. Louis, Mo.) by centrifugation at 450 g for 30 minutes. Cells were stimulated with 1 nM chTNT-3, chTNT-3/IL-2 fusion protein, or chTNT-3/IL-2 mutant fusion protein at $1\times10^6$ cells/mL in a 5% $CO_2$ humidified 37° C. incubator. AIM-V serum-free lymphocyte media (Life Technologies, Rockville, Md.) was utilized to eliminate the effect of serum on cytokine induction. Supernatants were collected after one, three, five, and seven days, centrifuged to remove remaining cells, and cytokine concentrations determined by ELISA following the manufacturer's protocol (Endogen, Inc., Woburn, Mass.). Absorbance was detected by spectrophotometry, and the concentration of cytokine was determined from a standard curve. The mean cytokine secretion was determined by standardizing the mutant-stimulating cytokine secretion as a percentage of the mean rhuIL-2-induced secretion for each day in each individual experiment. The sensitivity of each ELISA varied from 3-10 pg/mL. The results are summarized in Table 4 and in FIGS. 4A-4C.

TABLE 4

Relative ability of chTNT-3/IL-2 and chTNT-3/IL-2 mutant fusion proteins to induce secondary cytokine production.

| | Secondary Cytokine Production | | |
|---|---|---|---|
| | IL-1β | IFN-γ | TNF-α |
| ChTNT-3 | – | – | – |
| ChTNT-3/Native IL-2 | + + + + | + + + + | + + + + |
| ChTNT-3/D20K IL-2 Mutant | –/+ | –/+ | –/+ |
| ChTNT-3/R38G IL-2 Mutant | + + | + + | + + |
| ChTNT-3/R38W IL-2 Mutant | + + | + + + + | + + |
| ChTNT-3/M39V IL-2 Mutant | + + + | + + + | + + + |
| ChTNT-3/M39L IL-2 Mutant | + + | + + + | + + |
| ChTNT-3/F42K IL-2 Mutant | –/+ | + | – |
| ChTNT-3/H55Y IL-2 Mutant | + + | + + + + | + + |
| ChTNT-3/N88R IL-2 Mutant | + | + + + | + |

Expressed as percent of native activity: – = no activity, + = less than 25% activity, + + = 25-50% activity, + + + = 51-75% activity, + + + + = 76-100%.

The results show that the D20K and F42K mutant IL-2/antibody fusion proteins were unable to elicit the production of the cytokines IL-1β, IFN-γ, and TNF-α, while the R38G, R38W, M39V, M39L, H55Y and N88R mutant IL-2/antibody fusion proteins retained 50% of the activity of the native IL-2/antibody fusion protein in inducing secondary cytokine production. The choice of replacement amino acid at the same position also effected secondary cytokine production. For example, the R38W mutant retained 76-100% of the activity of the native IL-2 fusion protein in inducing IFN-γ production, while the R38G mutant retained only 25-50% of the activity of the native IL-2 fusion protein.

E. Determination of Lymphokine-Activated Killer (LAK) Cell Activity. The purified antibody/IL-2 fusion proteins were examined for their ability to stimulate LAK cell activity. PBMC were cultured at $1\times10^6$ cells/mL in AIM-V medium in the presence of 1 nM chTNT-3, rhuIL-2, chTNT-3/IL-2 fusion protein, or chTNT-3/IL-2 mutant fusion protein and incubated at 37° C. in a humidified 5% $CO_2$ atmosphere. AIM-V (Life Technologies, Inc., Rockville, Md.) is a chemically defined serum-free media designed to support the growth of lymphocytes in the absence of serum, thereby avoiding the serum-induced activation of PBMC. After 72 hours, the cells were harvested, washed, and incubated with Daudi lymphoma cells in four hour cytotoxicity assays. Lactate dehydrogenase (LDH) release was measured with the Promega Cyto Tox96 Non-Radioactive Cytotoxicity Assay. Spontaneous LDH release from target and effector cells were both subtracted from the measured values and the final results were expressed in percent specific cytotoxicity. The results shown in FIGS. 5A-5C indicate that the R38G and the R38W antibody/IL-2 mutant fusion proteins were capable of activating PBMC to generate LAK activity.

Example 3

Characterization of IL-2 Mutant Polypeptide Activities In Vivo

This example provides methods of determining the in vivo activity of chimeric antibody/IL-2 fusion proteins (mutant or native). Specifically, this example provides methods for determining the toxicity and immunotherapeutic properties of IL-2 fusion proteins.

A. Determination of IL-2 Vasopermeability Activity. In order to determine whether the IL-2 mutant polypeptides exhibited reduced toxicity, vasopermeability activity was monitored in vivo. Six-week old BALB/c nu/nu mice were inoculated subcutaneously in the left flank with approximately $1\times10^7$ LS174T human colorectal carcinoma cells.

Approximately 10 days later, when the tumors had reached approximately 0.5-1.0 cm in diameter, the mice were injected intravenously with a 0.1 mL inoculum containing 25 µg of chTNT-3 antibody alone, chTNT-3/native IL-2 fusion protein, or chTNT-3/IL-2 mutant fusion protein (n=5/group). Two hours later, the animals were injected with a 0.1 mL inoculum of $^{125}$I-B72.3, an antibody that recognizes TAG-72, a tumor associated glycoprotein highly expressed on human colorectal carcinoma. Animals were sacrificed by sodium pentobarbital overdose three days post-injection and blood, tumor, and various organs were removed and weighed. The radioactivity in the samples was then measured in a gamma counter and the data for each mouse were expressed as median percent injected dose/gram (% ID/g) and median tumor:organ ratio (cpm per gram tumor/cpm per gram organ). Vasopermeability was expressed as the percent of the pretreatment-mediated increase in B72.3 uptake (% ID/g) over pretreatment with chTNT-3 antibody alone. Wilcoxon rank sum analysis was performed to detect statistically significant differences in the biodistribution of the molecules (p 0.05).

TABLE 5

Vasopermeability Analysis of chTNT-3/IL-2 and chTNT-3/IL-2 Mutant Fusion Proteins.

| Pretreatment | Vasopermeability Induction (% ± sd) |
|---|---|
| chTNT-3 | 0 ± 5 |
| chTNT-3/IL-2 Native | 100 ± 15 |
| chTNT-3/D20K IL-2 Mutant | −28 ± 6 |
| chTNT-3/R38G IL-2 Mutant | −7 ± 15 |
| chTNT-3/R38W IL-2 Mutant | 4 ± 16 |
| chTNT-3/R38Y IL-2 Mutant | 42 ± 8 |
| chTNT-3/R38E IL-2 Mutant | −5 ± 6 |
| chTNT-3/M39V IL-2 Mutant | 99 ± 27 |
| chTNT-3/M39L IL-2 Mutant | 52 ± 23 |
| chTNT-3/F42K IL-2 Mutant | 97 ± 31 |
| chTNT-3/H55Y IL-2 Mutant | −6 ± 6 |
| chTNT-3/N88R IL-2 Mutant | 98 |

The results summarized in Table 5 show that the D20K, R38G, R38W, R38E and H55Y antibody/IL-2 mutant fusion proteins exhibit substantially reduced vasopermeability activity in vivo as compared to the native IL-2 antibody fusion protein. This is in contrast to the N88R mutant which retains full vasopermeability activity.

B. Determination of Toxicity of Native And R38W Mutant IL-2 Antibody Fusion Proteins. The general comparative toxicity of the R38W mutant antibody fusion protein as compared to the native IL-2 antibody fusion protein was determined in normal 8 week-old female BALB/c mice. Mice are much less susceptible to IL-2 toxicity than humans. For these studies, groups of 5 mice received increasing concentrations of fusion protein (10-75 µg) by daily intravenous 0.1 mL inoculums for five consecutive days. Acute toxicity was measured by the death of the mice.

TABLE 6

Toxicity of native and mutant IL-2 antibody fusion proteins in BALB/c mice treated intravenously for five consecutive days.

| Fusion Protein* | 10 µg | 25 µg | 50 µg | 75 µg | 100 µg |
|---|---|---|---|---|---|
| ChTNT-3/IL-2 (wt) | 0/5 | 2/5 | 5/5 | 5/5 | 5/5 |
| ChTNT-3/R38W | 0/5 | 0/5 | 0/5 | 2/5 | 5/5 |
| ChTNT-3/N88R | 0/5 | 0/5 | 0/5 | 0/5 | 0/5 |

*Data expressed as number of mice dead over total number injected.

The results in Table 6 show that the native IL-2 antibody fusion protein was acutely toxic in animals receiving the 25 µg dose and the higher doses of 50 µg and 75 µg resulted in the death of all 5 mice in each group. By contrast, the R38W mutant antibody fusion protein exhibited decreased toxicity since only 2/5 mice died at the highest dose of 75 µg. These data demonstrate that the R38W mutant IL-2 shows significantly lower general toxicity than native IL-2. The N88R IL-2 mutant was even less toxic that R38W, with all animals surviving even at a dose of 100 µg.

In addition, the half-life of the antibody/IL-2 fusion protein was approximately 12-18 hours compared to free IL-2 which has a half-life of about 20 minutes after intravenous administration. This shows that the IL-2 mutant antibody fusion protein is capable of prolonged administration in vivo while remaining less toxic than native IL-2.

C. Immunotherapy of Solid Tumor with Native and R38W Mutant IL-2 Antibody Fusion Proteins. In order to determine the comparative immunotherapeutic effect of the R38W mutant antibody fusion protein compared to the native IL-2 antibody fusion protein, the proteins were administered to normal 6 week-old female BALB/c mice which had been inoculated subcutaneously with $10^7$ viable MAD 109 lung carcinoma cells. After 5 days, when the tumors reached approximately 0.5 cm in diameter, groups of 5 mice received intravenous treatment for four consecutive days with increasing doses of either chTNT-3/native IL-2 or chTNT-3/R38W mutant IL-2 fusion protein using a 0.1 mL inoculum given once on days 5-8. Control mice received no treatment or antibody alone. Volumetric measurements of tumor size were made three times a week starting at the time of the first therapeutic dose.

Figure 6A:
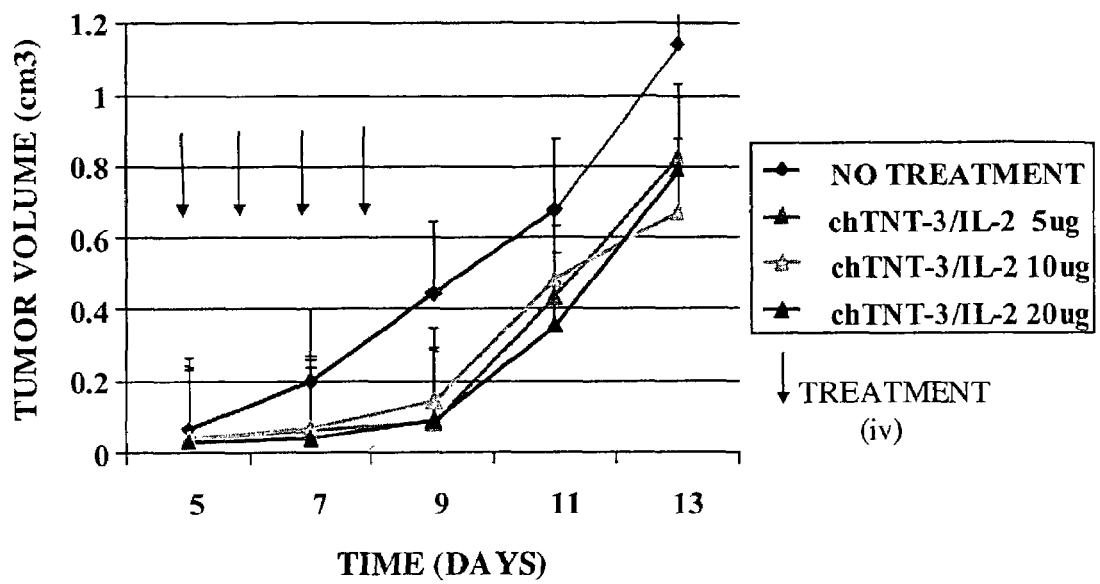
FIGS. 6A-6B show tumor therapy using various antibody-IL-2 fusion constructs.
Figure 6B:
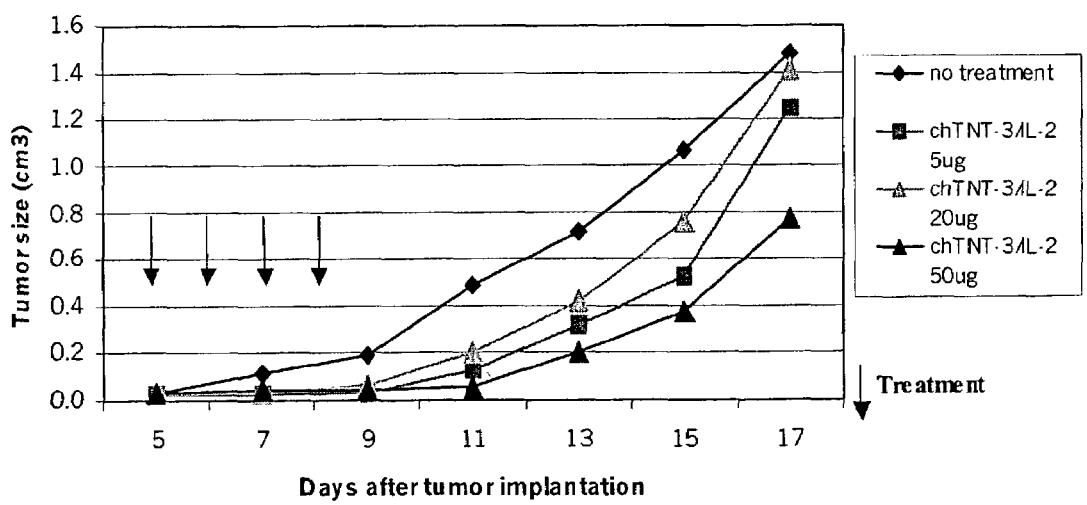
Figure 7A:
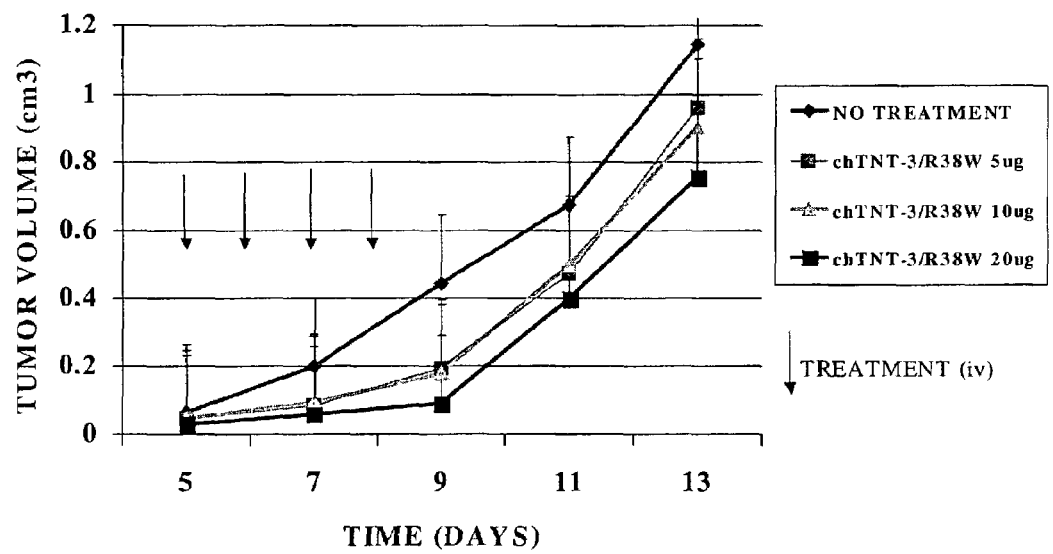
FIGS. 7A-7B show tumor therapy using various antibody-IL-2 fusion constructs.
Figure 7B:
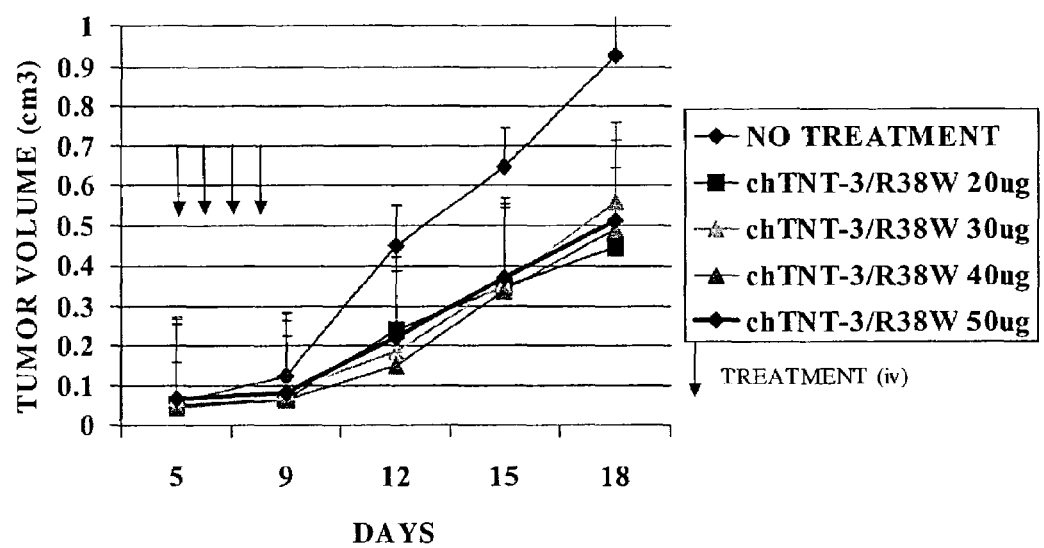
Figure 8:
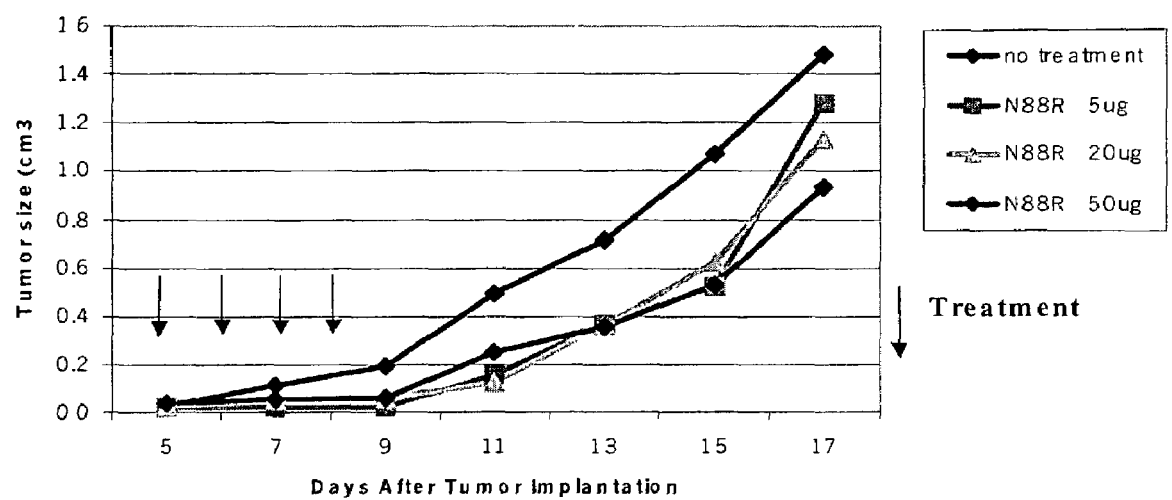
FIGS. 8 shows tumor therapy using chTNT-3/N88R protein (5-50 μg) as compared to no treatment.

The results are shown in FIGS. 6-8. As shown in FIGS. 6A and 6B, the native IL-2 antibody fusion protein administered to MAD 109 tumor bearing BALB/C mice showed a marked and similar decrease in tumor size at the all doses up through days 5-9. Thereafter, the tumors began to increase in size at roughly the same rate as untreated controls except at the highest dose (50 µg).

FIG. 7A show that groups of mice receiving lower doses (5-20) of the R38W mutant IL-2/antibody fusion protein also showed similar curves as the mice treated with the native IL-2 antibody fusion protein. In contrast, FIG. 7B shows that mice treated with higher doses of R38W (20-50 µg) showed a slower rate of growth compared to the control mice after discontinuation of therapy (see decreased slope in FIG. 7B versus that of FIG. 6B).

FIG. 8 shows tumor immunotherapy for the N88R IL-2 mutant at the 5, 20 and 50 µg dose. Slightly improved therapeutic affect was observed for this mutant at the 50 µg dose as compared to native IL-2 fusion protein. Thus, these data demonstrate that significantly higher doses of the R38W and N88R mutant IL-2 fusion protein can be used to achieve a tumor immunotherapeutic effect that are possible with native IL-2 fusion protein. The ability to use increased doses with reduced toxicity allowed greater tumor therapeutic effect with the low vasopermeability IL-2 mutants than the native IL-2.

While the invention has been described in detail with reference to certain preferred embodiments thereof, it will be understood that modifications and variations are within the spirit and scope of that which is described and claimed. The present invention may suitably be practiced in the absence of any element or limitation not specifically disclosed herein. The terms and expressions employed herein have been used as terms of description to facilitate enablement and not of limitation, and there is no intention in the use of such terms

That which is claimed is:

1. An interleukin-2 (IL-2) mutant with reduced vasopermeability activity compared to a wildtype form of the IL-2 mutant, said mutant being Arg38Trp, said mutant also comprising a mutation at one or more of positions outside the permeability enhancing peptide region of IL-2, wherein said permeability enhancing peptide region of IL-2 represents position 22 to 58 of IL-2, wherein said wildtype form of the human IL-2 mutant is human IL-2 and wherein said IL-2 mutant is not linked to an antibody.

2. The IL-2 mutant of claim 1, wherein said mutant comprises a full-length IL-2 molecule.

3. A method of producing a low toxicity interleukin-2 (IL-2) in a form suitable for administration in vivo, said method, comprising formulating the IL-2 mutant of claim 1 with at least one pharmaceutically acceptable carrier.

4. A human interleukin-2 (IL-2) mutant with reduced vasopermeability activity compared to a wildtype form of the IL-2 mutant, said mutant being Arg38Trp and containing a mutation at one or more of positions outside the permeability enhancing peptide region of IL-2, wherein said permeability enhancing peptide region of IL-2 represents position 22 to 58 of IL-2.

5. The IL-2 mutant of claim 4, wherein said mutant comprises a full-length IL-2 molecule.

6. A method of producing a low toxicity interleukin-2 (IL-2) in a form suitable for administration in vivo, said method, comprising formulating the IL-2 mutant of claim 4 with at least one pharmaceutically acceptable carrier.

7. Purified human interleukin-2 (IL-2) which has a tryptophan residue in place of an arginine residue at position 38 said IL-2 also comprising a mutation at one or more of positions outside the permeability enhancing peptide region of IL-2, wherein said permeability enhancing peptide region of IL-2 represents position 22 to 58 of IL-2.

8. The IL-2 of claim 7 which comprises 133 amino acids.

9. A method of producing a low toxicity interleukin-2 (IL-2) in a form suitable for administration in vivo, said method, comprising formulating the IL-2 mutant of claim 7 with at least one pharmaceutically acceptable carrier.

10. A pharmaceutical composition comprising human interleukin-2 (IL-2) which has a tryptophan residue in place of an arginine residue at position 38 said mutant also comprising a mutation at one or more of positions outside the permeability enhancing peptide region of IL-2, wherein said permeability enhancing peptide region of IL-2 represents position 22 to 58 of IL-2.

11. The composition of claim 10 wherein the IL-2 comprises 133 amino acids.

* * * * *